United States Patent
Bredno

(10) Patent No.: US 8,565,371 B2
(45) Date of Patent: Oct. 22, 2013

(54) ROTATIONAL X RAY DEVICE FOR PHASE CONTRAST IMAGING

(75) Inventor: Joerg Bredno, San Francisco, CA (US)

(73) Assignee: Koninklijke Philips N.V., Eindhoven (NL)

( * ) Notice: Subject to any disclaimer, the term of this patent is extended or adjusted under 35 U.S.C. 154(b) by 261 days.

(21) Appl. No.: 12/933,143

(22) PCT Filed: Mar. 13, 2009

(86) PCT No.: PCT/IB2009/051051
§ 371 (c)(1),
(2), (4) Date: Dec. 8, 2010

(87) PCT Pub. No.: WO2009/115966
PCT Pub. Date: Sep. 24, 2009

(65) Prior Publication Data
US 2011/0261924 A1    Oct. 27, 2011

(30) Foreign Application Priority Data

Mar. 19, 2008 (EP) .................................. 08152971

(51) Int. Cl.
*A61B 6/03* (2006.01)

(52) U.S. Cl.
USPC ............................................................. 378/9

(58) Field of Classification Search
USPC ............................................... 378/4, 5, 9, 19
See application file for complete search history.

(56) References Cited

U.S. PATENT DOCUMENTS

| | | | |
|---|---|---|---|
| 5,812,629 A | 9/1998 | Clauser | |
| 6,850,595 B2 | 2/2005 | Zhou et al. | |
| 7,486,770 B2* | 2/2009 | Baumann et al. | 378/62 |
| 7,864,415 B2* | 1/2011 | McNulty | 359/370 |
| 8,155,273 B2* | 4/2012 | Eaton et al. | 378/136 |

(Continued)

FOREIGN PATENT DOCUMENTS

| | | |
|---|---|---|
| EP | 1731099 A1 | 12/2006 |
| JP | 2006255089 A | 9/2006 |

(Continued)

OTHER PUBLICATIONS

Weitkamp et al: "X-Ray Phase Imaging With a Grating Interferometer"; Optics Express, August 2005, Vol. 13, No. 16, pp. 6296-6304.

(Continued)

*Primary Examiner* — Irakli Kiknadze

(57) ABSTRACT

The invention relates to a rotational X-ray device (100), for example a CT scanner, for generating phase contrast images of an object (1). In a particular embodiment of the device (100), a plurality of X-ray sources (11), an X-ray detector (30), and an analyzer grating ($G_2$) are attached to a rotatable gantry (20), while a ring-shaped phase grating ($G_1$) is stationary. The X-ray sources are disposed such that X-rays first pass an object under study before traversing the phase grating ($G_1$) and subsequently the analyzer grating ($G_2$). This is achieved by either shifting the X-ray sources axially with respect to the ring-shaped phase grating ($G_1$) or by disposing the X-ray sources in the interior of the ring. Moreover, the phase grating ($G_1$) and the analyzer ($G_2$) shall have spatially varying relative phase (and/or periodicity), for example realized by line grids that are tilted with respect to each other. During the rotation of the gantry (20), the synchronized activation of X-ray sources (11) allows to generate projection images of an object (1) from the same viewing angle with different relative positions (and therefore phases) between the phase grating ($G_1$) and the analyzer ($G_2$).

20 Claims, 5 Drawing Sheets

(56) References Cited

U.S. PATENT DOCUMENTS

| | | |
|---|---|---|
| 2002/0094064 A1 | 7/2002 | Zhou et al. |
| 2007/0183559 A1 | 8/2007 | Hempel |
| 2007/0183560 A1 | 8/2007 | Popescu et al. |
| 2007/0183580 A1 | 8/2007 | Popescu et al. |
| 2007/0183583 A1 | 8/2007 | Baumann et al. |

FOREIGN PATENT DOCUMENTS

| | | |
|---|---|---|
| JP | 2007097610 | 4/2007 |
| WO | 2004058070 A1 | 7/2004 |
| WO | 2007087789 A1 | 8/2007 |

OTHER PUBLICATIONS

Pfeiffer et al: "Phase Retrieval and Differential Phase-Contrast Imaging With Low Brilliance X-Ray Sources"; Nature Physics, vol. 2, April 2006, pp. 258-261.

Momose, A.: "Phase-Sensitive Imaging and Phase Tomography Using X-Ray Interferometers"; Optics Express, September 2003, vol. 11, No. 19, pp. 2303-2314.

Yue et al: "Generation of Continuous and Pulsed Diagnostic Imaging X-Ray Radiation Using a Carbon-Nanotube-Based Filed-Emission Cathode": Applied Physics Letters, Vol. 81, No. 2, July 2002, pp. 355-357.

* cited by examiner t = t₁ t = t₂

ROTATIONAL X RAY DEVICE FOR PHASE CONTRAST IMAGING

FIELD OF THE INVENTION

The invention relates to a method and a rotational X-ray device for generating phase contrast X-ray images of an object. Moreover, it relates to a computer program product incorporating such a method.

BACKGROUND OF THE INVENTION

While classical X-ray imaging measures the absorption of X-rays caused by an object, phase contrast imaging aims at the detection of the phase shift X-rays experience as they pass through an object. According to a design that has been described in literature (T. Weitkamp et al., "X-ray phase imaging with a grating interferometer", Optics Express 13(16), 2005), a phase grating is placed behind an object to generate an interference pattern of intensity maxima and minima when the object is irradiated with (coherent) X-rays. Any phase shift in the X-ray waves that is introduced by the object causes some characteristic displacement in the interference pattern. Measuring these displacements therefore allows to reconstruct the phase shift of the object one is interested in.

A problem of the described approach is that the feasible pixel size of existing X-ray detectors is (much) larger than the distance between the maxima and minima of the interference pattern. These patterns can therefore not directly be spatially resolved. To deal with this issue, it has been proposed to use an absorption grating immediately in front of the detector pixels, thus looking only at small sub-sections of the interference pattern with the pixels of the detector. Shifting the absorption grating with respect to the pixels allows to recover the structure (i.e. the deviation from the default pattern without an object) of the interference pattern. The necessary movement of optical elements is however a nontrivial mechanical task, particularly if it has to be done fast and with high accuracy, as would be required if phase contrast imaging shall be applied in a medical environment.

BRIEF DESCRIPTION OF THE INVENTION

Based on this background it was an object of the present invention to provide means for generating X-ray phase contrast images of an object that are particularly suited for an application in medical imaging, for example in computed tomography (CT).

This object is achieved by a rotational X-ray device according to claim 1, a method according to claim 14, and a computer program product according to claim 15. Preferred embodiments are disclosed in the dependent claims.

The rotational X-ray device according to the present invention serves for the generation of phase contrast images of an object, i.e. images in which the value of image points is related to the phase shift that is induced in transmitted X-rays by the object, while the position of image points is spatially related to the object (e.g. via a projection or section mapping). As the term "rotational" indicates, the X-ray device shall be designed in such a way that a relative rotation between the object and the viewing angle of generated (projection-) images is possible. The X-ray device comprises the following components:

a) At least two X-ray sources for generating X-rays. The X-ray sources are preferably selectively controllable, i.e. they can for example be activated sequentially and/or independently of each other. Moreover, it is preferred that more than just two X-ray sources are available, with a typical number lying between three and eight X-ray sources.

b) A diffractive optical element, which will be abbreviated "DOE" in the following. The DOE is exposed to the X-ray sources, i.e. it is disposed such that it is hit by the emission of the X-ray sources if the latter are active.

c) An X-ray detector for detecting interference patterns that are generated by the DOE. To this end, the X-ray detector is disposed behind the DOE as seen from the viewing point of the X-ray sources.

d) An analyzer that is disposed in front of the X-ray detector for modulating the spatial sensitivity of this detector corresponding to a periodicity of the DOE (e.g. having substantially twice the periodicity of the DOE). The application of such an analyzer is particularly useful in combination with usual X-ray sensitive elements (e.g. pixels comprising a scintillator with an associated photodetector or pixels comprising a directly converting material) because the latter have a size which is typically much larger than the pitch of an interference pattern. In this case, the analyzer can be used to increase the spatial resolution of the X-ray detector to the limit given by the periodicity of the interference pattern. The analyzer may for example be realized by an absorption grating or by a scintillation structure as described in US 2007/0183580 A1.

Furthermore, the X-ray device shall have the following features:

The X-ray sources, the X-ray detector, and (only) one of the DOE and the analyzer are commonly rotatable about a rotation axis relative to a centre region where the object can be placed. As either the DOE or the analyzer does not take part in such a rotation (but usually remains stationary with respect to the object), there will be a relative rotation between the DOE and the analyzer. Moreover, it should be noted that the rotation of the X-ray sources, X-ray detector and DOE/analyzer is only RELATIVE to the centre region; with respect to the environment, the enumerated components may remain stationary (while the centre region with the object makes an absolute movement).

The DOE and the analyzer have a relative phase and/or a relative periodicity that varies when they are rotated with respect to each other about the rotation axis. In this context, the "phase" and "periodicity" refer to optically active structures of the DOE and the analyzer, respectively, for example a pattern of parallel lines in the case of line gratings. Moreover, the variation is judged with respect to at least one fixed location on the DOE or the analyzer and the corresponding nearest point on the other optical element (wherein said nearest point will change according to the relative rotation of the elements).

By rotating the X-ray sources, the X-ray detector and the DOE or the analyzer relative to an object, the device allows to generate X-ray projection images of an object from different directions. As the DOE and the analyzer rotate relative to each other, the relative phase and/or periodicity between DOE and analyzer will change for a given line of sight through the object during such an acquisition procedure. Thus it is possible to realize a relative shift between DOE and analyzer via a single (rotational) movement. The plurality of X-ray sources allows in this context to sequentially acquire X-ray projection images with different relative positions of the DOE and analyzer along a given line of sight, for example by activating each of the X-ray sources when it passes a particular position in space.

It should be noted that the "rotational" imaging of the device may for example be realized by rotating the object relative to a stationary imaging setup, by rotating the imaging setup relative to a stationary object, or by rotating the image generating activities (e.g. active X-ray source or readout pixels) in a stationary hardware relative to a stationary object. To simplify the discussion, it will in the following usually be assumed without loss of generality that the X-ray sources, the X-ray detector, and the DOE/analyzer rotate relative to the environment while the centre region with the object is stationary.

In principle, the X-ray detector may have one single sensitive element allowing to make a measurement in a corresponding sensitive area. Preferably the detector comprises however an array with a plurality of X-ray sensitive elements (pixels), particularly a one- or two-dimensional array. Measurements can then be made simultaneously at a plurality of positions, allowing for example to sample a spatially resolved two-dimensional projection image in one step.

The diffractive optical element DOE may be any device that is able to generate the desired interference pattern when irradiated with X-rays. Preferably, the DOE comprises a phase grating, i.e. a grating the lines of which have negligible absorption but substantial phase shift, thus minimizing the loss of X-ray photons.

The variable phase and/or periodicity between the DOE and the analyzer with respect to a relative revolution about the rotation axis may be realized in many ways. In a preferred embodiment, the DOE and the analyzer comprise identical or similar patterns, for example grids of parallel lines repeated with a given periodicity, wherein at first one of these patterns is (slightly) tilted or inclined with respect to a plane normal to the rotation axis. The relative phase between the patterns will therefore continuously change if the tilted first pattern rotates about the rotation axis. The second pattern may be oriented rotationally invariant with respect to the rotation axis, or it may also be tilted with respect to a plane normal to the rotation axis. In the latter case, the inclination of the second pattern may be different from that of the first pattern (i.e. the two patterns are also tilted with respect to each other). Preferably, the tilt will however be the same as for the first pattern because the DOE and the analyzer will then for any point in time have a constant relative phase/periodicity along the circumference about the rotation axis.

In another embodiment of the X-ray device, the DOE or the analyzer extends on a ring circumferentially about the rotation axis. Such a design of a closed ring is preferably chosen for the component (DOE or analyzer) that does not commonly rotate with the X-ray sources and X-ray detector; this component may then remain stationary with respect to the environment (which is mechanically the most simple solution) as it is perpetually in the optical path from the X-ray sources to the detector. Projection images of the object can in this case be generated in a full 360° range.

In the aforementioned case of a ring-shaped DOE or analyzer, care should be taken that the X-rays pass through said ring only behind (and not in front of) the object. To this end, the X-ray sources are preferably disposed axially (i.e. along the rotation axis) shifted with respect to said ring, with their emission being inclined towards the centre region. Additionally or alternatively, the X-ray sources may be disposed in the interior of said DOE or analyzer ring.

The at least two X-ray sources are preferably disposed on an arc about the rotation axis. This guarantees that two X-ray sources will sequentially assume the same position relative to the centre region/object when the imaging setup rotates. The two X-ray sources can therefore generate X-ray projections from exactly the same viewing angle relative to an object.

The X-ray sources may optionally comprise at least one cathode with carbon nanotubes for emitting electrons that generate X-rays when being bombarded onto a target. Carbon nanotubes have been shown to be excellent electron emitting materials which allow fast switching times with a compact design. Thus it is for example possible to build X-ray sources with multiple cathodes and/or stationary CT scanners. More information on carbon nanotubes and X-ray sources that can be built with them can be found in literature (e.g. US 2002/0094064 A1, U.S. Pat. No. 6,850,595, or G. Z. Yue et al., "Generation of continuous and pulsed diagnostic imaging x-ray radiation using a carbon-nanotube-based field-emission cathode", Appl. Phys. Lett. 81(2), 355-8 (2002), which are included into the present text by reference).

The X-ray device may further optionally comprise a control unit for triggering the acquisition of an X-ray exposure when a first X-ray source and a second X-ray source, respectively, pass a given spatial position relative to the centre region. X-ray projections having similar viewing angles but different relative settings of the DOE and analyzer can thus be generated.

It was already mentioned that the X-ray sources should have the temporal and spatial coherence that is necessary for the generation of an interference pattern behind the DOE. The X-ray sources may optionally comprise a spatially extended emitter that is disposed in front of a grating, wherein the term "in front of" refers to a viewing point located in the X-ray source. The extended emitter can be a standard anode as it is used in conventional X-ray sources and may by itself be spatially incoherent. With the help of the grating, the emitter is effectively divided in a number of line emitters each of which is spatially coherent (in a direction perpendicular to its length).

The X-ray device preferably further comprises an evaluation unit for determining the phase shift caused by an object that is disposed in the path of the X-rays between the X-ray sources and the DOE. The evaluation unit may optionally be realized by dedicated electronic hardware, digital data processing hardware with associated software, or a mixture of both. The evaluation unit exploits the fact that there is a well-defined relationship between the phase shift induced by an object and the resulting changes in the interference pattern that can be observed behind the DOE; inverting this relationship allows to calculate the desired phase contrast image of the object.

In a further development of the aforementioned embodiment, the evaluation unit additionally comprises a reconstruction module for reconstructing cross-sectional phase contrast images of an object from (phase contrast) projections of said object which were taken from different directions. The reconstruction module may apply algorithms of computed tomography (CT) which are well-known for a person skilled in the art of absorption X-ray imaging. Additionally or alternatively, the reconstruction module may be adapted to reconstruct absorption images of the object from projections of different directions.

The invention further relates to a method for generating phase contrast images of an object, the method comprising the following steps:
a) Irradiating said object with a first X-ray source selected from a plurality of X-ray sources.
b) Generating an interference pattern with a diffractive optical element, called "DOE", disposed behind the object (wherein the term "behind" refers to a viewing point located in the first X-ray source).

c) Sampling the aforementioned interference pattern with an X-ray detector through an analyzer that modulates the spatial sensitivity of the detector corresponding to a periodicity of the DOE.

d) Rotating the plurality of X-ray sources, the X-ray detector, and either the DOE or the analyzer synchronously relative to the object about a rotation axis, thereby changing the relative phase and/or periodicity of the DOE and the analyzer.

e) Repeating steps a), b), and c) with a second X-ray source selected from the plurality of X-ray sources when this second X-ray source assumes the position that was assumed in the previous step a) by the first X-ray source.

The X-ray device will typically be programmable, e.g. it may include a microprocessor or an FPGA. Accordingly, the present invention further includes a computer program product which provides the functionality of any of the methods according to the present invention when executed on a computing device.

Further, the present invention includes a data carrier, for example a floppy disk, a hard disk, or a compact disc (CD-ROM), which stores the computer product in a machine readable form and which executes at least one of the methods of the invention when the program stored on the data carrier is executed on a computing device.

Nowadays, such software is often offered on the Internet or a company Intranet for download, hence the present invention also includes transmitting the computer product according to the present invention over a local or wide area network. The computing device may include a personal computer or a work station. The computing device may include one of a microprocessor and an FPGA.

The above method, computer program product, data carrier and transmission procedure comprise as an essential component the concept of the X-ray device described above. Reference is therefore made to the above description for more information about the details, advantages and modifications of these elements.

BRIEF DESCRIPTION OF THE DRAWINGS

These and other aspects of the invention will be apparent from and elucidated with reference to the embodiment(s) described hereinafter. These embodiments will be described by way of example with the help of the accompanying drawings in which.

Like reference numbers in the Figures refer to identical or similar components.

DESCRIPTION OF EMBODIMENTS

Phase contrast X-ray imaging aims at the measurement of the phase shift of X-rays as they pass through an object. The benefit of phase sensitive measurements is that the phase contrast is potentially orders of magnitude higher than the absorption contrast (cf. A. Momose, "Phase sensitive imaging and phase tomography using X-ray interferometers", Optics Express 11(19), 2003; T. Weitkamp et al., "X-ray phase imaging with a grating interferometer", Optics Express 13(16), 2005). Initially a major shortcoming of phase sensitive methods was that X-ray sources with a very narrow bandwidth were required. This shortcoming could however be overcome by using standard X-ray tubes with a special filter to achieve a bandwidth of 10%-20% (cf. F. Pfeiffer et al., "Phase retrieval and differential phase contrast imaging with low-brilliance X-ray sources", Nature Physics 2, pp 258-261, 2006). When combined with phase stepping, phase sensitive measurements and total X-ray absorption information can be obtained while using polychromatic X-ray sources.

In order to measure the phase of X-rays with the known setups, at least three independent measurements of each geometrical ray are required, where at least one of several grids has to be displaced perpendicular to the optical axis by fractions of its grid constant. Tomography may be performed in these approaches using a rotating object, where the measurements are taken at a stationary relative position of the measurement setup. However, for a medical tomography system, it is mandatory that the data acquisition is performed using a system that rotates continuously around the object (patient). Furthermore, in a medical tomography system grid movements need to be performed not only precisely, but also rather quickly, which is very hard to perform.

FIGS. 1 to 4 illustrate an X-ray device 100 that addresses the above issues. The X-ray device 100 comprises an X-ray source module 10 for generating X-radiation. The X-ray source module 10 comprises in a casing a plurality of spatially extended X-ray sources 11, 11' that can for example be realized by the focus (anode) of a "broadband" X-ray source and that typically have an extension of several millimeters perpendicular to the optical axis (y-axis). Moreover, it is preferred that carbon nanotubes (CNT) are used for the corresponding cathodes as this allows tube designs with fast switching and large anodes. A grating $G_0$ is disposed in front of the X-ray sources 11, 11' to subdivide the emission in lines each of which is spatially coherent in transverse (z-) direction. More details about this approach can be found in literature (e.g. Pfeiffer et al., above).

Figure 1:
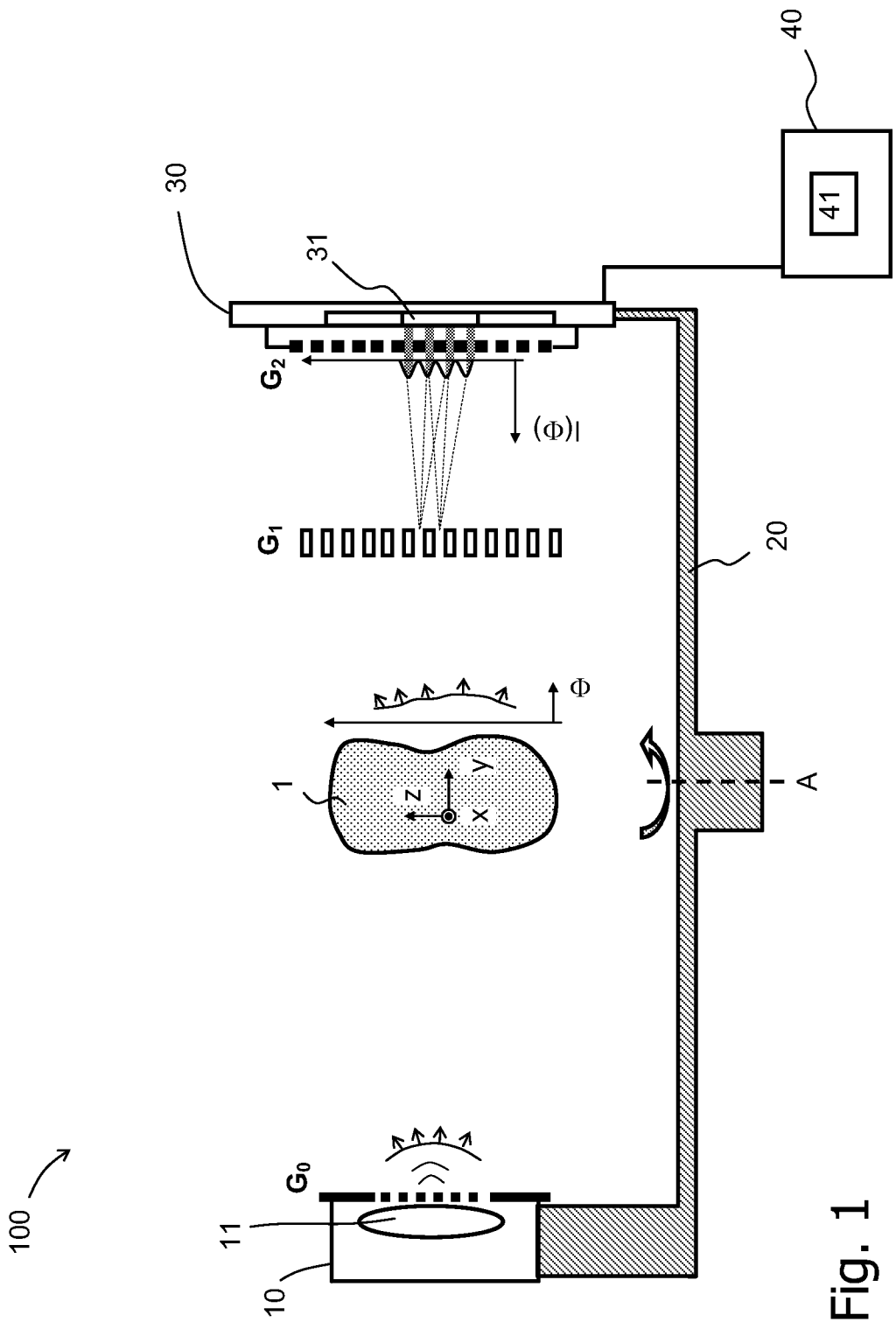
FIG. 1 shows schematically a rotational X-ray device according to the present invention in a section along the y-axis of FIG. 2.

For purposes of clarity, only one cylindrical wave propagating in y-direction beyond one slit of the grating $G_0$ is illustrated in FIG. 1. The cylindrical wave passes through an object 1, for example the body of a patient, that is located in a center region (around the origin of the x,y,z-coordinate system) and that shall be imaged by the device 100. The material of the object 1 induces a phase shift in the X-ray wave, resulting in an altered (disturbed) wave front behind the object 1. For each position z perpendicular to the optical (y-) axis, a phase shift $\Phi(z)$ is thus associated to the wave front that is characteristic of the material properties along the corresponding X-ray path. The complete function $\Phi$ is a phase contrast projection image of the object 1 one is interested in.

In order to determine the phase shift function $\Phi$, a diffractive optical element (DOE) is disposed behind the object 1. In the shown example, this DOE is realized by a beam splitter phase grating $G_1$ extending perpendicular to the optical axis (with its slits parallel to the slits of the source grating $G_0$). The grating $G_1$ generates an interference pattern in transmission geometry, i.e. in the space opposite to the object side. This interference pattern can, at fixed coordinates y and x, be characterized by an intensity function I(z, Φ).

At a given distance from the DOE grating $G_1$, the interference pattern will correspond to a periodic pattern of intensity maxima and minima as schematically illustrated in FIG. 1. Measuring this interference pattern with an X-ray detector 30 will then allow to infer the phase shifts Φ(z) that were introduced by the object 1.

In practice, the measurement of the interference pattern I at a distance from the grid $G_1$ is however a nontrivial task as the required spatial resolution, determined by the distance between two adjacent maxima or minima, is much smaller than the size of the sensitive elements or pixels 31 of usual X-ray detectors. To address this problem, it has been proposed in literature to place an analyzer immediately in front of the detector pixels 31. This analyzer is here realized by an absorption grating $G_2$ having essentially the same periodicity as the grid $G_1$ behind the object. The absorption grating $G_2$ has the effect to provide small windows through which the detector "looks" at corresponding subsections of the periodic interference pattern I, for example at small regions around the maxima, thus effectively measuring the intensity in these subsections. By shifting the analyzer grating $G_2$ in z-direction, the interference pattern might be sampled at several positions, which would allow to reconstruct it completely together with the local X-ray absorption. A problem of such a grid-stepping approach is that it requires a complicated and precise mechanics. To avoid this problem, the rotational X-ray device 100 realizes the following features:

It comprises a plurality of X-ray sources 11, 11' disposed on an arc about the rotation axis A (z-axis in the Figures).

The X-ray sources 11, 11', the pixelated X-ray detector 30, and the analyzer grating $G_2$ are attached to a rotatable gantry 20.

The phase grating $G_1$ is stationary and extends as a complete ring (only partially shown in the Figures) around the centre region with the object 1.

The relative pattern-phase of the phase grating $G_1$ and the analyzer grating $G_2$ change in circumferential direction about the rotation axis A.

Figure 2:
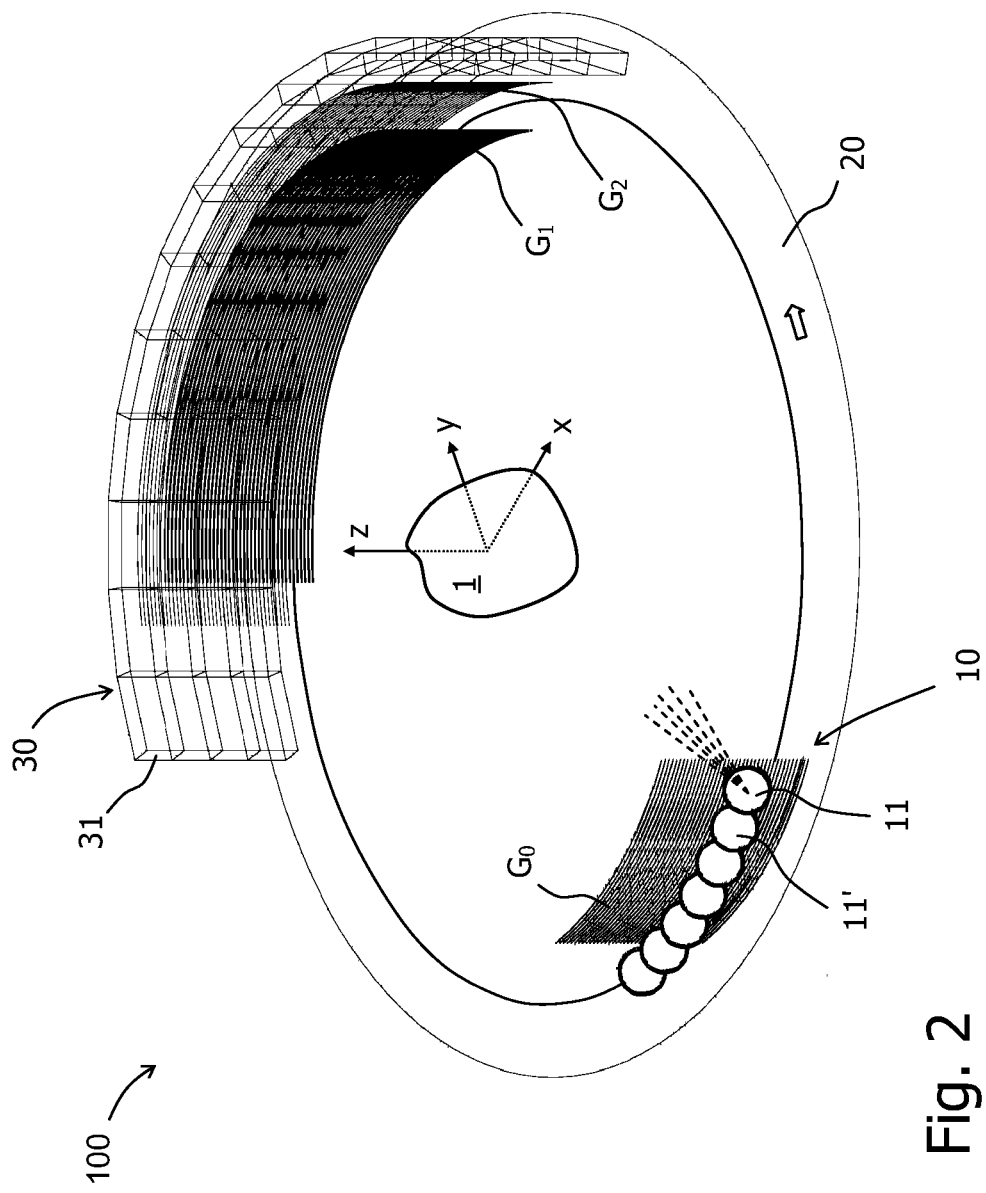
FIG. 2 shows the X-ray device schematically in a perspective view.

FIG. 2 illustrates the relative spatial arrangement of the mentioned components in a schematic perspective view. When the DOE $G_1$ is a complete ring extending over 360°, the X-ray beams must pass the source grating $G_0$ but not the DOE grating $G_1$ on the source side. This is either implemented with a slight axial offset (as in 4th generation CT gantries) or by placing the small, possibly CNT-based emitters on the inside of the static phase grating ring.

Figure 3:
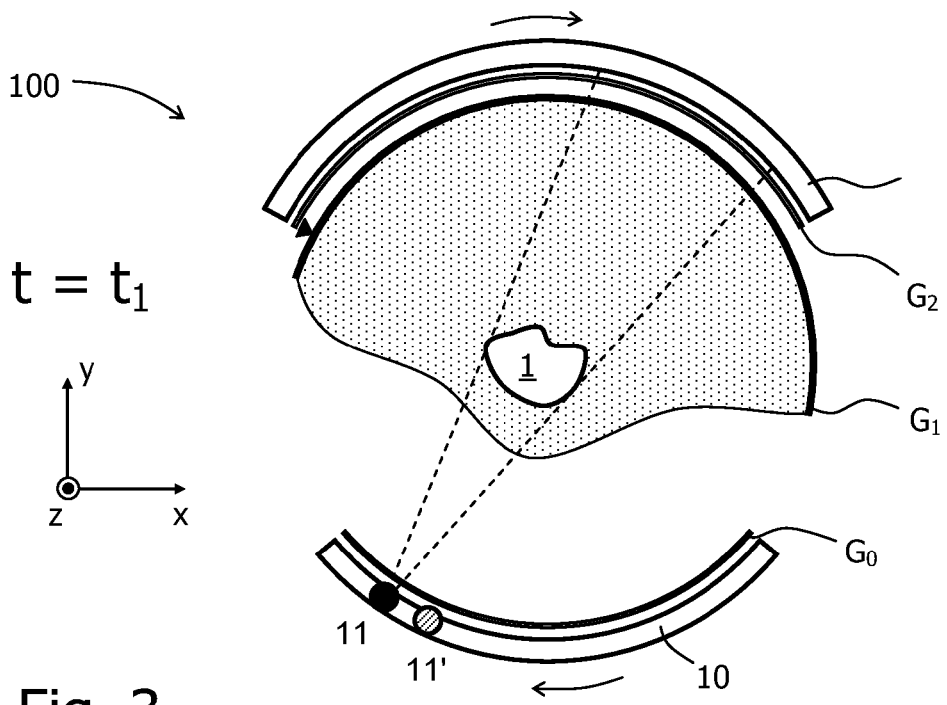
FIG. 3 shows the X-ray device schematically in a top view at a first point in time when a first projection of an object is generated with a first X-ray source.
Figure 4:
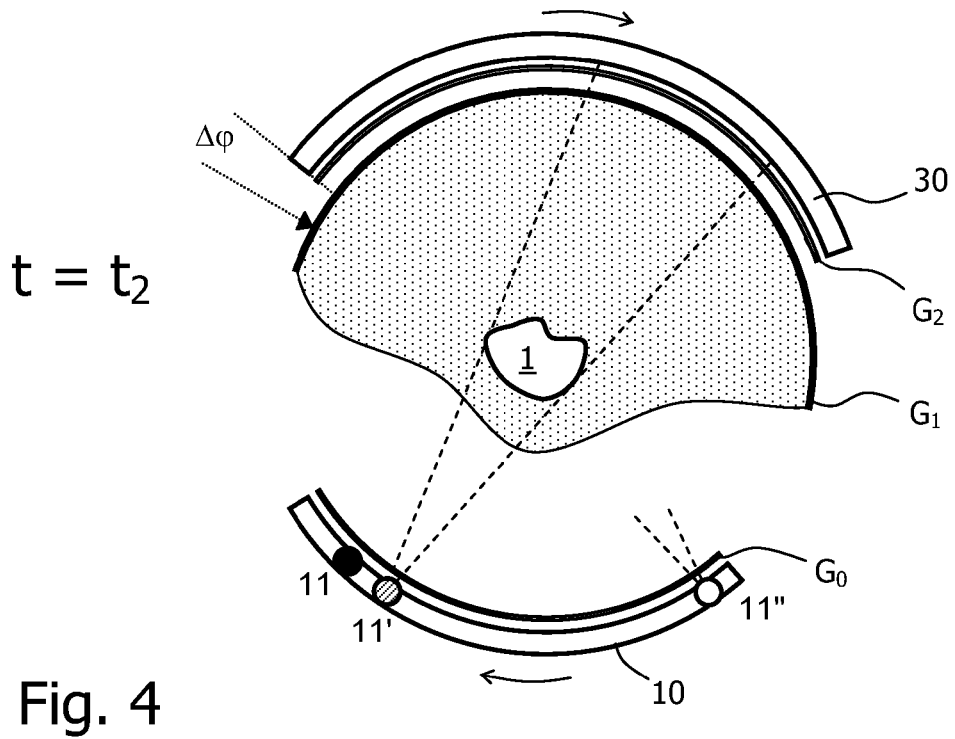
FIG. 4 shows the same setup as FIG. 3 at a later point in time when a second projection of the object is generated with a second X-ray source from the same viewing angle.

FIGS. 3 and 4 illustrate the operation of the described X-ray device 100 in more detail. In FIG. 3, the positions of the gantry components (X-ray sources 11, 11', detector 30, analyzer $G_2$) relative to the stationary components (phase grating $G_1$ and object 1) are shown at a first point in time $t_1$. A first X-ray source 11 is activated in this case by the control and evaluation unit 40, irradiating the object 1 from a particular viewing angle and generating a projection image on the opposite section of the detector 30. The phase grating $G_1$ and the analyzer $G_2$ assume a particular relative angular position at this moment.

FIG. 4 shows the same components at a later point in time $t_2$. The gantry 20 has rotated for an angle Δφ such that a second X-ray source 11' now assumes the spatial position which the first X-ray source 11 had at time $t_1$. When the second X-ray source 11' is activated by the control and evaluation unit 40, it will therefore irradiate the (stationary) object 1 from the same viewing angle as the first X-ray source 11 did at time $t_1$. The relative position between the phase grating $G_1$ and the analyzer $G_2$ has however changed by the rotational angle Δφ in the second exposure. By a proper design of the phase grating $G_1$ and the analyzer grating $G_2$, this relative movement of the gratings can just realize the relative shift of the gratings that is needed for phase contrast imaging with phase stepping.

As indicated in FIG. 4b) by a third X-ray source 11", multiple X-ray sources may be active at the same time in a simultaneous exposure and detector readout if they have sufficient angular distance to irradiate mutually separate sensitive areas on the detector.

Figure 5:
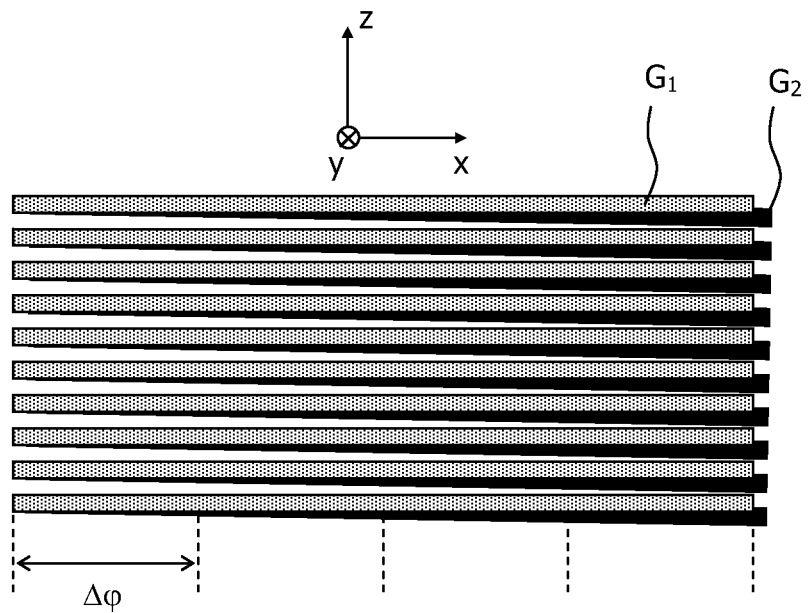
FIG. 5 illustrates a DOE and an analyzer tilted with respect to each other.

FIG. 5 illustrates a first possible realization of the phase grating $G_1$ and the analyzer grating $G_2$. Both gratings are defined by a pattern of parallel lines (phase shifting lines in the case of the phase grating $G_1$ and absorbing lines in the case of the analyzer $G_2$). The lines have the same periodicity, but they are slightly tilted with respect to each other out of the slice orientation. More particularly, the lines of the rotated grating (the analyzer $G_2$ in this case) are tilted with respect to the (x,y) plane normal to the rotation axis A (otherwise a rotation of the lines would change nothing), while the lines of the stationary grating ($G_1$) may be parallel to this plane.

The Figure shows that a relative rotation between the two gratings about the aforementioned angle Δφ will change the relative phases of the line patterns. The tilt is selected such that a rotation by the angle covered by the X-ray sources results in a relative shift of analyzer and phase gratings of one lattice parameter: For the reconstruction of a phase contrast image from a particular viewing angle, a number N of (usually three or eight) projections with different relative phases of the phase grating $G_1$ and analyzer grating $G_2$ have to be made. The inclination of the gratings is therefore chosen such that 1/N-th of a full period shift between the line patterns is made after each rotational step Δφ of the gantry.

Figure 6:
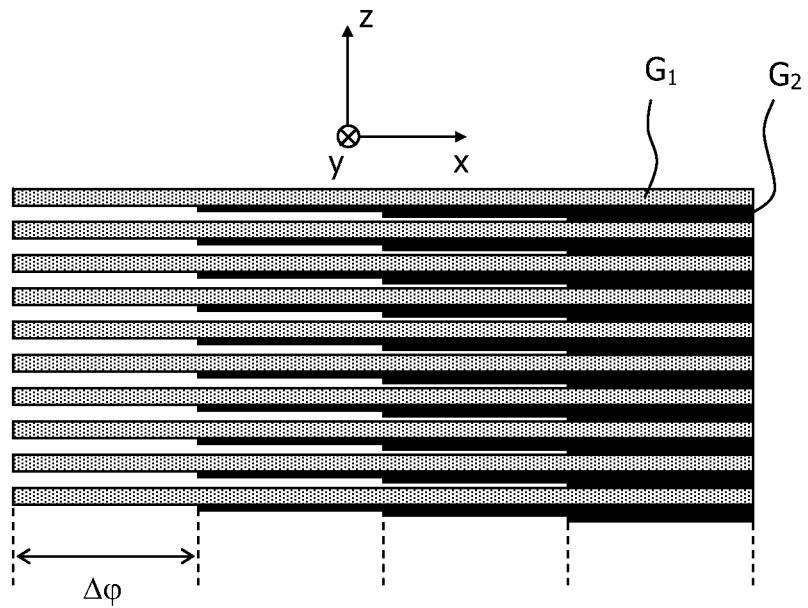
FIG. 6 illustrates a DOE and an analyzer with discrete steps of relative phase shift.

FIG. 6 illustrates an alternative embodiment of the phase grating $G_1$ and the analyzer $G_2$, in which the lines of the analyzer grating $G_2$ are shifted in z-direction in discrete steps.

Figure 7:
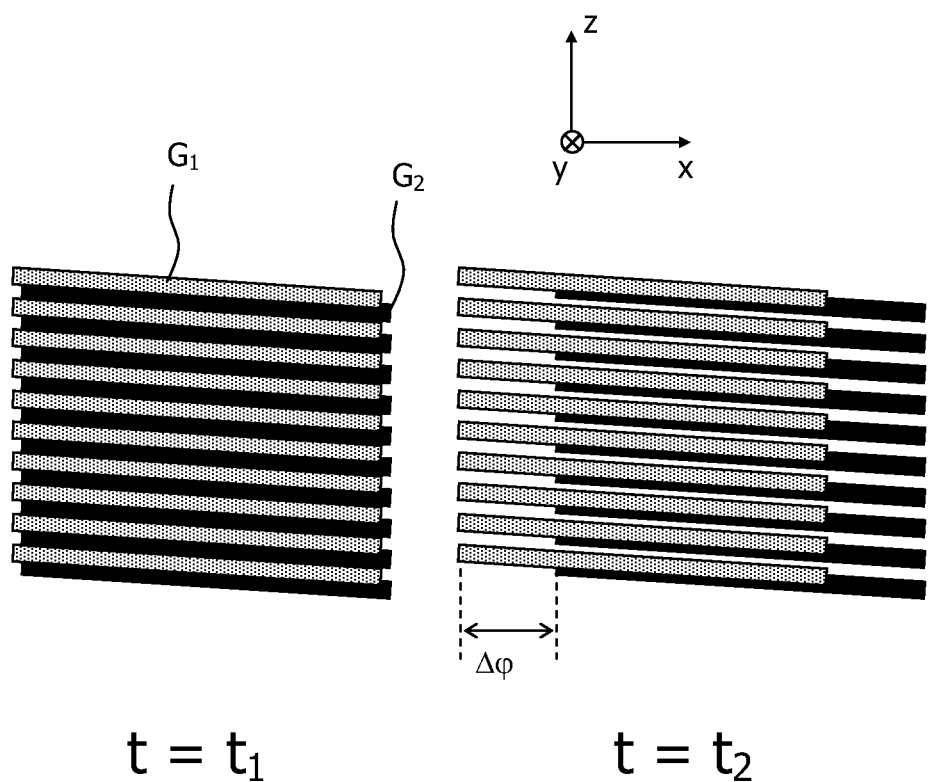
FIG. 7 illustrates a DOE and an analyzer at two different points in time which are tilted in the same way with respect to a plane normal to the rotation axis.

FIG. 7 illustrates for two points $t_1$, $t_2$ in time a third embodiment of the phase grating $G_1$ and the analyzer $G_2$. In this case both gratings are tilted in the same way (i.e. for the same angle) with respect to the (x,y) plane normal to the rotation axis A (z-axis). A shift of the analyzer $G_2$ for the rotation angle Δφ will therefore change from time point $t_1$ to time point $t_2$ the relative phase between the two gratings homogenously across the whole detector area. This spatial homogeneity of conditions facilitates the following reconstruction procedure with the projections acquired at certain points in time.

In summary, a geometry and setup for a differential phase contrast CT with phase stepping has been proposed where only the rotation of a gantry is mechanically realized and no additional mechanically moved parts are required. The setup uses a phase grating ring $G_1$ attached on a stator and an analyzer grating $G_2$ attached to the rotating gantry. By tilting both grids $G_1$, $G_2$ in a small angle, the relative shift of the gratings is implemented by the rotation of the gantry itself. Multiple X-ray sources 11, 11' distributed on the diameter of the gantry image the same rotation angle with different relative positions of phase and analyzer gratings. For acquisition and reconstruction, the gantry is rotated while the X-ray sources are switched fast and synchronized to the rotation. Each combination of source and detector can contribute to the acquired Radon projection space. Additionally, under the same Radon angle, different sources acquire the same projection with different relative position of analyzer and phase gratings. Sorting of the projections results in Radon spaces for all different relative shifts of the gratings, which is input to reconstruction.

Finally it is pointed out that in the present application the term "comprising" does not exclude other elements or steps, that "a" or "an" does not exclude a plurality, and that a single processor or other unit may fulfill the functions of several means. The invention resides in each and every novel characteristic feature and each and every combination of characteristic features. Moreover, reference signs in the claims shall not be construed as limiting their scope.

The invention claimed is:

1. A rotational X ray device for generating phase contrast images of an object, comprising:
    a) at least two X ray sources;
    b) a diffractive optical element that is exposed to the X ray sources;
    c) an X ray detector for detecting interference patterns generated by the diffractive optical element;
    d) an analyzer disposed in front of the X ray detector that modulates a spatial sensitivity of the X ray detector corresponding to a periodicity of the diffractive optical element;
    wherein the X ray sources, the X ray detector, and either the diffractive optical element or the analyzer are rotatable about a rotation axis relative to a center region where the object is located; the diffractive optical element or the analyzer extends on a ring circumferentially about the rotation axis; and the diffractive optical element and the analyzer have a relative phase and/or periodicity that varies when they are rotated with respect to each other about the rotation axis.

2. The X ray device according to claim 1, wherein the X ray detector comprises an array of X ray sensitive elements.

3. The X ray device according to claim 1, wherein the diffractive optical element comprises a phase grating.

4. The X ray device according to claim 1, wherein the analyzer comprises an absorption grating.

5. The X ray device according to claim 1, wherein the diffractive optical element and the analyzer comprise identical or similar optical patterns of which at least one is tilted with respect to a plane (x, y) normal to the rotation axis.

6. The X ray device according to claim 1, wherein the X ray sources are disposed axially shifted with respect to said ring and/or in the interior of said ring.

7. The X ray device according to claim 1, wherein the X ray sources are disposed on an arc about the rotation axis.

8. The X ray device according to claim 1, wherein at least one X ray source comprises at least one cathode with carbon nanotubes.

9. The X ray device according to claim 1, further comprising:
    a control unit for triggering the acquisition of an X ray exposure when a first and a second X ray source, respectively, pass a given position relative to the center region.

10. The X ray device according to claim 1, wherein at least one of the X ray sources comprises a spatially extended emitter disposed in front of a grating.

11. The X ray device according to claim 1, further comprising:
    an evaluation unit for determining the phase shift caused by an object in the path of the X rays from the X ray sources to the X ray detector.

12. The X ray device according to claim 11, wherein the evaluation unit comprises a reconstruction module for reconstructing a cross-sectional phase contrast image and/or an absorption image of an object from projections of the object taken from different directions.

13. A method for generating phase contrast images of an object, comprising the following steps:
    a) irradiating the object with a first X ray source from a plurality of X ray sources;
    b) generating an interference pattern with a diffractive optical element behind the object;
    c) sampling the interference pattern with an X ray detector through an analyzer key that modulates the spatial sensitivity of the detector corresponding to a periodicity of the diffractive optical element;
    d) rotating the plurality of X ray sources, the X ray detector, and either the diffractive optical element or the analyzer synchronously rotate about a rotation axis relative to the object, thereby changing the relative phase and/or periodicity of the diffractive optical element and the analyzer, wherein the diffractive optical element or the analyzer extends on a ring circumferentially about the rotation axis; and
    e) repeating steps a) to c) with a second X ray source of the plurality of X ray sources at same positions of the first X ray source.

14. The method of claim 13, wherein the diffractive optical element comprises a phase grating.

15. The method of claim 13, wherein the analyzer comprises an absorption grating.

16. The method of claim 13, wherein the X ray sources are disposed axially shifted with respect to the ring and/or in the interior of the ring.

17. A data carrier which stores a computer program product in a machine readable, which, when executed by a microprocessor, the microprocessor to:
    a) irradiate an object with a first X ray source from a plurality of X ray sources;
    b) generate an interference pattern with a diffractive optical element behind the object;
    c) sample the interference pattern with an X ray detector through an analyzer that modulates the spatial sensitivity of the detector corresponding to a periodicity of the diffractive optical element;
    d) rotate the plurality of X ray sources, the X ray detector, and either the diffractive optical element or the analyzer synchronously rotate about a rotation axis relative to the object, thereby changing the relative phase and/or periodicity of the diffractive optical element and the analyzer, wherein the diffractive optical element or the analyzer extends on a ring circumferentially about the rotation axis; and
    e) repeat steps a) to c) with a second X ray source of the plurality of X ray sources at same positions of the first X ray source.

18. The data carrier of claim 17, wherein the diffractive optical element comprises a phase grating.

19. The data carrier of claim 17, wherein the analyzer comprises an absorption grating.

20. The data carrier of claim 17, wherein the X ray sources are disposed axially shifted with respect to the ring and/or in the interior of the ring.

* * * * *